United States Patent [19]

Wei et al.

[11] 4,443,606
[45] Apr. 17, 1984

[54] ANTIVIRAL THIAZOLO [5,4-B] PYRIDINE COMPOUNDS

[75] Inventors: Peter H. L. Wei, Springfield; Stanley C. Bell, Penn Valley, both of Pa.

[73] Assignee: American Home Products Corporation, New York, N.Y.

[21] Appl. No.: 388,856

[22] Filed: Jun. 16, 1982

[51] Int. Cl.$^3$ ............................................ C07D 513/04
[52] U.S. Cl. .................................. 546/114; 424/256; 424/270; 548/172
[58] Field of Search ......................... 546/114; 548/172

[56] References Cited

U.S. PATENT DOCUMENTS 4,275,605  6/1981  Wei et al. ............................ 546/114

FOREIGN PATENT DOCUMENTS 2135543  1/1973  Fed. Rep. of Germany .
41-17215  9/1966  Japan .

OTHER PUBLICATIONS

Sycheva et al., Khim.-Farm.Zh., 1969, vol. 3, (No. 8), pp. 18-21,-Chem. Abstracts, vol. 72 (1970); 31703x.

Primary Examiner—Henry R. Jiles
Assistant Examiner—Bernard Dentz
Attorney, Agent, or Firm—George Tarnowski

[57] ABSTRACT

Thioacetonitriles and other derivatives of benzo- and azabenzothiazoles and their use as antiviral agents are disclosed.

2 Claims, No Drawings

ANTIVIRAL THIAZOLO [5,4-B] PYRIDINE COMPOUNDS

The invention relates to thioacetonitriles and other derivatives of benzo- and azabenzothiazoles and their use as antiviral agents.

The invention is directed to novel compounds having the general formula

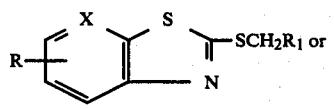

or

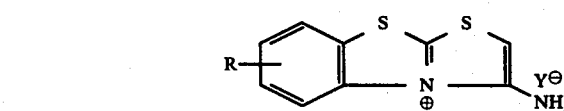

wherein
R is hydrogen, chlorine or bromine;
$R_1$ is CN or

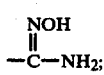

X is CH or N; and
Y is chloride or bromide, with the proviso that when X=CH,

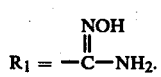

The compounds having the formula

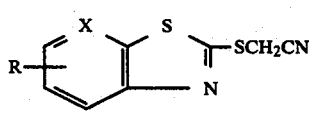

can be prepared by reacting a 2-mercaptobenzothiazole or 2-mercaptoazabenzothiazole of the formula

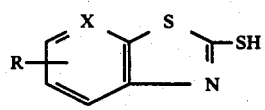

wherein R and X are as defined hereinbefore, with chloroacetonitrile to furnish the desired thioacetonitrile derivative. In order to prepare the compounds in which $R_1$ is to be the N-hydroxyethanimidamide group, the appropriate thioacetonitrile derivative

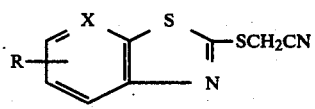

is reacted with hydroxyamine as follows:

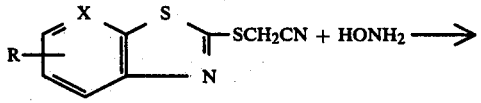

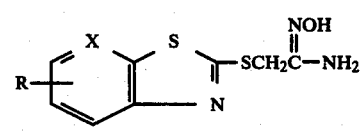

The compounds of the formula

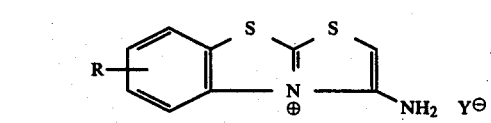

can be prepared by cyclizing an appropriate benzothiazolylthioacetonitrile with a cyclizing agent, preferably a hydrogen halide and most preferably hydrogen chloride:

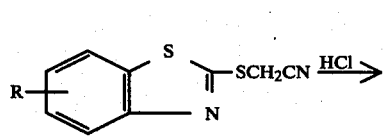

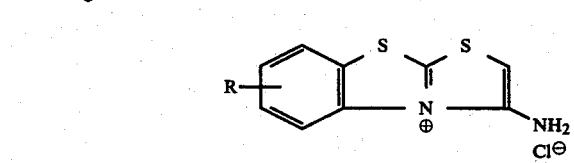

The starting 2-mercaptobenzothiazoles and 2-mercaptoazabenzothiazoles are commercially available or can be conveniently prepared by conventional known methods.

The compounds of the invention have antiviral activity and can be used against DNA and RNA viruses in humans and other mammals. For this purpose, they can be formulated into oral dosage forms such as tablets, capsules and the like. The compounds can be administered alone or by combining them with conventional carriers, such as magnesium carbonate, magnesium stearate, talc, sugar, lactose, pectin, dextrin, starch, gelatin, tragacanth methyl cellulose, sodium carboxymethyl cellulose, low melting wax, cocoa butter, and the like. Diluents, flavoring agents, solubilizers, lubricants, suspending agents, binders, tablet-disintegrating agents and the like may be employed. The compounds may be encapsulated with or without other carriers. In all cases the proportion of active ingredients in said compositions both solid and liquid will be at least sufficient to impart antiviral activity thereto on oral administration. The compounds may also be injected parenterally, in which case they are used in the form of a sterile solution containing other solutes, for example, enough saline or glucose to make the solution isotonic.

The antiviral activity of the compounds of the invention may be demonstrated in standard procedures which are more fully described in the examples given hereinafter.

The following examples show the preparation of the compounds of the invention.

EXAMPLE 1

(5-Chloro-2-benzothiazolylthio)acetonitrile 51.0 g (0.254 m), 5-chloro-2-mercaptobenzothiazole, 22.8 g (0.304 m) chloroacetonitrile and 30.7 g triethylamine are dissolved in 600 ml of toluene and the solution is heated to reflux for 3 hr, then allowed to cool to room temperature. The toluene solution is washed with water, dried over anhydrous magnesium sulfate and treated with Darco. After the solvent is removed, the residual solid is recrystallized from 300 ml. benzene. The recovered material is recrystallized from cyclohexane. A total yield of 52 g (86%) is obtained. The recrystallized sample has a melting point of 96°-7° C.

Analysis for: $C_9H_5ClN_2S_2$: Calculated: C, 44.91; H, 2.09; Cl, 14.73; N, 11.64; Found: C, 45.05; H, 2.10; Cl, 14.74; N, 11.58

EXAMPLE 2

2-(5-Chloro-2-benzothiazolylthio)-N-hydroxy-ethanimidamide 14.4 g (0.6 m) (5-chloro-2-benzothiazolylthio)acetonitrile, prepared according to Example 1, 4.17 g (0.06 m) hydroxyamine hydrochloride and 4.14 g (0.03 m) potassium carbonate are dissolved in a mixture of 180 ml ethanol and 2 ml water. The mixture is heated overnight and then cooled. The solid which is collected is washed with water. The crude material is recrystallized from ethanol. The recrystallized product weighs 5.6 g (34% yield) and melts at 155°-7° C.

Analysis for: $C_9H_8ClN_3OS_2$: Calculated: C, 39.48; H, 2.95; Cl, 12.95; N, 15.35; S, 23.43; Found: C, 39.66; H, 3.15; Cl, 12.94; N, 15.35; S, 23.63

EXAMPLE 3

(5-Chloro-thiazolo[5,4-b]pyridin-2-ylthio)acetonitrile

The title compound is prepared in 58% yield following the procedure in Example 1 and by substituting 5-chloro-2-mercaptothiazolo[5,4-b]pyridine for 5-chloro-2-mercaptobenzothiazole. The compound is recrystallized from acetonitrile and ethanol in succession and has a melting point of 112°-4° C.

Analysis for: $C_8H_4ClN_3S_2$: Calculated: C, 39.75; H, 1.67; N, 17.38; Found: C, 39.61; H, 1.68; N, 17.53

EXAMPLE 4

3-Amino-6 chlorothiazolo[2,3-b]benzothiazolium chloride

Dry hydrochloride is bubbled into a solution of 12.0 g (0.05 m) (5-chloro-2-benzothiazolylthio)acetonitrile, prepared according to Example 1, in 100 ml methylene chloride and 100 ml ethanol for ½ hr. The mixture is cooled in an ice bath and the collected solid is recrystallized from a mixture of 200 ml ethanol and 250 ml water. The compound weighs 9.5 g (68% yield) and has a melting point of 193°-5° C.

Analysis for: $C_9H_6ClN_2S_2Cl$: Calculated: C, 38.99; H, 2.18; Cl, 10.17; N, 25.58; Found: C, 38.94; H, 1.90; Cl, 10.34; N, 25.53

EXAMPLE 5

The compounds of the invention are tested in vitro against Rhinovirus strains (such as Rhinovirus 1A(2060), 52 (F0-I3772), 2(HCP) and 34) according to the following protocol Human embryonic lung cells (cell strains Wi38), seeded in growth medium into each of 96 wells in a plastic disposable tissue culture plate, are grown to confluency and are then refed with maintenance medium. Four dilutions of a test compound are then added to each of four wells in a plate at final concentrations of 50, 10, 1.0 and 0.1 µg/cup/ml. and the plate is then incubated. If no compound toxicity for the cells is evident after 24 hours at 37° C., all wells are then inoculated with 100 $TCID_{50}$ of Rhinovirus. The plates are then sealed with scotch tape and reincubated at 33°-34° C. Antiviral activity is recorded by the inhibition of typical Rhinovirus cell cytopathology in the wells containing the test compound as compared to control wells not containing compound. The scoring of a test commences when there is at least a 50% cytopathic effect in the virus control wells. Uninoculated, cell controls are also included in each plate to assure that nonspecific cell degeneration has not occurred.

In this test, of the compounds of the invention the compound 2-(5-chloro-2-benzothiazolylthio)-N-hydroxy-ethanimidamide showed a significant activity.

EXAMPLE 6

The compounds of the invention are tested in vivo against the DNA virus *Herpes Simplex* and against the RNA viruses Influenza B-Mass. and $A_2$ Taiwan according to the following protocol Ten 12-14 gm. mice are treated with each dilution of a test compound 24 hours prior to and at 1, 24, 48 and 72 hours after the inoculation of a standardized challenge dose of test virus. Mice are inoculated intraperitoneally with the compound dilution and intranasally with either of the two Influenza viruses and subcutaneously with compound dilution and intraperitoneally with Herpes virus. Twenty mice, inoculated with saline instead of the test compound, serve as the control group. All mice are observed for 21 days and the number of deaths occurring in each group recorded. Antiviral activity of a compound is scored statistically for significance at the 95 and 99% confidence levels on the basis of percentage of survivors and prolongation of life.

In this test, of the compounds of the invention, the compound 3-amino-6-chlorothiazolo[2,3-b]benzothiazolium chloride showed significant activity against *Herpes simplex* while the compound (5-chlorothiazolo[5,4-b]pyridin-2-ylthio)acetonitrile showed significant activity against Influenza B-Mass.

What is claimed is:

1. A compound of the formula

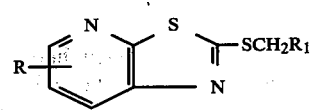

wherein R is hydrogen, chlorine or bromine, and

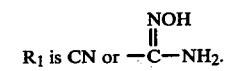

2. The compound of claim 1, which is (5-chlorothiazolo[5,4-b]pyridin-2-ylthio)acetonitrile.

* * * * *